United States Patent [19]

Benz

[11] Patent Number: 5,127,278

[45] Date of Patent: Jul. 7, 1992

[54] APPARATUS FOR DISSOLUTION TESTING OF SOLID MEDICATIONS

[75] Inventor: Reinhard Benz, Basel, Switzerland

[73] Assignee: Sotax AG, Basel, Switzerland

[21] Appl. No.: 625,217

[22] Filed: Dec. 10, 1990

[30] Foreign Application Priority Data

Dec. 18, 1989 [CH] Switzerland ............. 4529/89

[51] Int. Cl.⁵ .................................................. G01N 33/15
[52] U.S. Cl. .................................................. 73/866
[58] Field of Search ................ 73/866, 38, 863.23, 73/863.24, 863.25, 863.31

[56] References Cited

U.S. PATENT DOCUMENTS

| | | | |
|---|---|---|---|
| 4,555,934 | 12/1985 | Freeman et al. | 73/38 |
| 4,573,342 | 3/1986 | Jones | 73/38 |
| 4,642,220 | 2/1987 | Björkman | 73/863.23 |
| 4,879,917 | 11/1989 | Eppelmann et al. | 73/866 |
| 4,924,716 | 5/1990 | Schneider | 73/866 |

FOREIGN PATENT DOCUMENTS 2530065  3/1977  Fed. Rep. of Germany ........ 73/866

*Primary Examiner*—Hezron E. Williams
*Assistant Examiner*—Howard Wisnia
*Attorney, Agent, or Firm*—Michael J. Striker

[57] ABSTRACT

An apparatus for dissolution testing of solid medications in accordance with a throughflow method comprises a plurality of testing cells to be surrounded by heating bath each having a lower supply opening for testing fluid and an upper filter with a filter head having an outlet opening, a connecting member arranged on the filter head and tightly connectable with the outlet opening of the filter head under pressure and connected with a conduit for outflow of the testing fluid, a cell base provided with a testing fluid supply conduit and tightly placed on the supply opening of each of the testing cells, and a tensioning unit pressing all the connecting members and all the cell bases together on the testing cells.

15 Claims, 4 Drawing Sheets

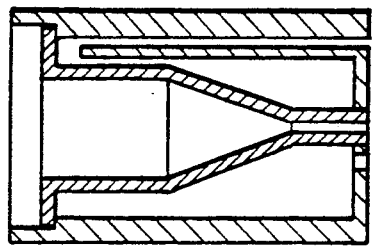
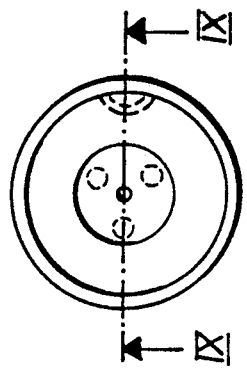
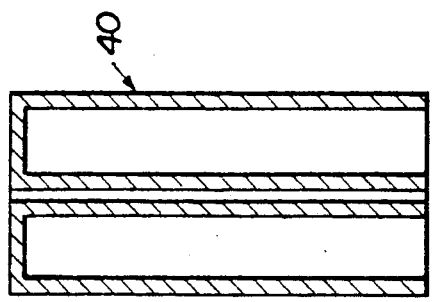
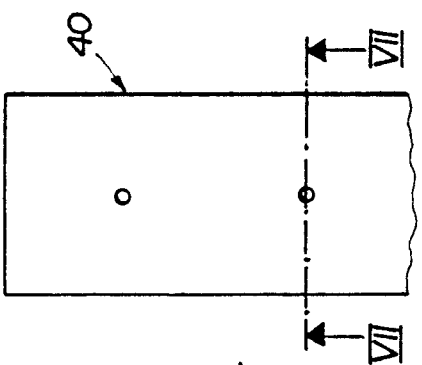
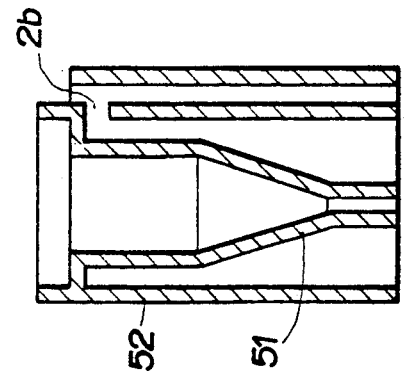
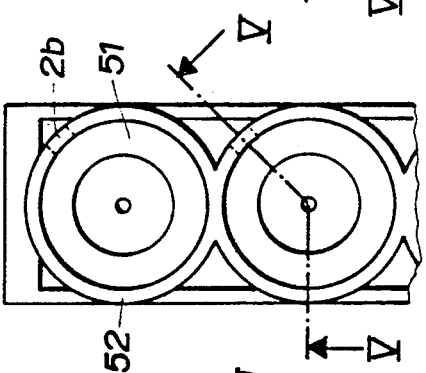
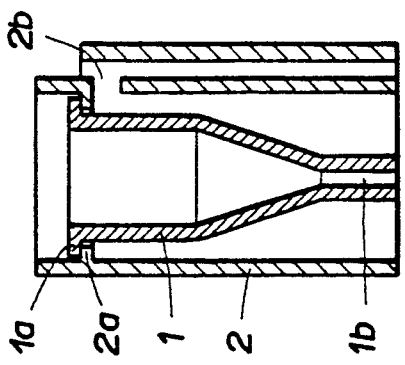
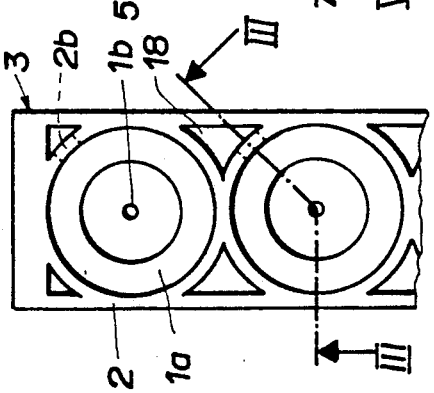

APPARATUS FOR DISSOLUTION TESTING OF SOLID MEDICATIONS

BACKGROUND OF THE INVENTION

The present invention relates to an apparatus for dissolution testing of solid medications in accordance with the through flow method.

Apparatuses of the above mentioned general type are known in the art. Such apparatuses have a plurality of testing cells surrounded by a plurality of testing baths or joint testing bath for maintaining a constant temperature. The testing cells are provided with a supply conduit for a testing fluid from below and with a filter with a removable filter head having an outlet opening from above. Testing fluid supply conduits for the testing cells and the thermostatically controlled heating water storage with a heating water supply conduit for the heating bath or the heating baths are also provide. The known devices of this type are suitable for simultaneous accommodation of three—ten, mainly for six—seven individual testing cells. Each of the cells is individually located in a casing tube for forming a heating bath. The cells are individually prepared by a laboratory operator and inserted in the apparatus and then each is closed with a filter head connected with the testing fluid discharge conduit. The filter heads are fixed in their places by the tensioning lever.

The above apparatus possesses the disadvantage in that after the course of an individual test, a short time test such as for example, an hour long test, the individual testing cells are changed or in other words, must be individually released from the tensioning device. The connecting conduits must be unscrewed from the filter heads and rinsed, and then again screwed on. Thus, the working time of the personnel is to be adjusted to the testing time of the research that makes harder a continuous work and can hardly cover a continuous 24 hour operation.

SUMMARY OF THE INVENTION

Accordingly, it is an object of the present invention to provide an apparatus of the above mentioned general type, which avoids the disadvantages of the prior art.

In keeping with these objects and with others which will become apparent hereinafter, one feature of the present invention resides, briefly stated, in an apparatus for dissolution testing of solid medications in which each testing cell is associated with a connecting member which is placeable on its filter head and tightly connectable with the outlet opening of the filter head under pressure, a testing fluid discharge conduit is connected with the connecting member, each testing cell is provided with a cell base having a testing fluid supply conduit to be tightly place on the supply opening of the testing cell, and a tensioning element is provided for pressing all connecting members and all cell bases together to the testing cells.

In such an apparatus the testing cells can be exchanged faster, whereby the time between the individual tests can be shortened. Furthermore, it is possible to use the apparatus as an automatically operating apparatus, in which the exchange of the testing cells is performed automatically. For this purpose a timer-controlled mechanism can be used. Such a mechanism can provide the following sequence of operations:

a cell element including several cells is brought to a position in which the supply openings of all cells are connected with testing fluid supply conduits and each heating bath is connected with a heating water supply conduit, the cell element is fixed by placing on the connecting piece, the heating water supply conduit is open and then the testing fluid throughflow is activated after elapse of an adjustable time the heating water circulation through the heating bath and the testing fluid supply are shut off, then the the connecting pieces are separated from the cells of the cell element, the conduits are rinsed and subjected to blowing, the cell element is removed, and then the next cell element is brought to the same position and all the steps are repeated until the apparatus is stopped or the element supply is arrested.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 3 is a view showing a vertical section through the testing cell, taken along the line III—III;

FIG. 4 is a plan view of a part of a cell unit;

FIG. 5 is a view showing a vertical section through a somewhat differently formed testing cell, taken along the line V—V;

FIG. 6 is a plan view of a part of the corresponding cell unit;

FIG. 7 is a view showing a section taken along the line VII—VII;

FIG. 8 is a plan view of a rinsing block of the inventive apparatus;

FIG. 9 is a vertical section taken along the line IX—IX;

FIG. 10 is a plan view of an individual testing cell;

DESCRIPTION OF THE PREFERRED EMBODIMENTS

Figure 2:
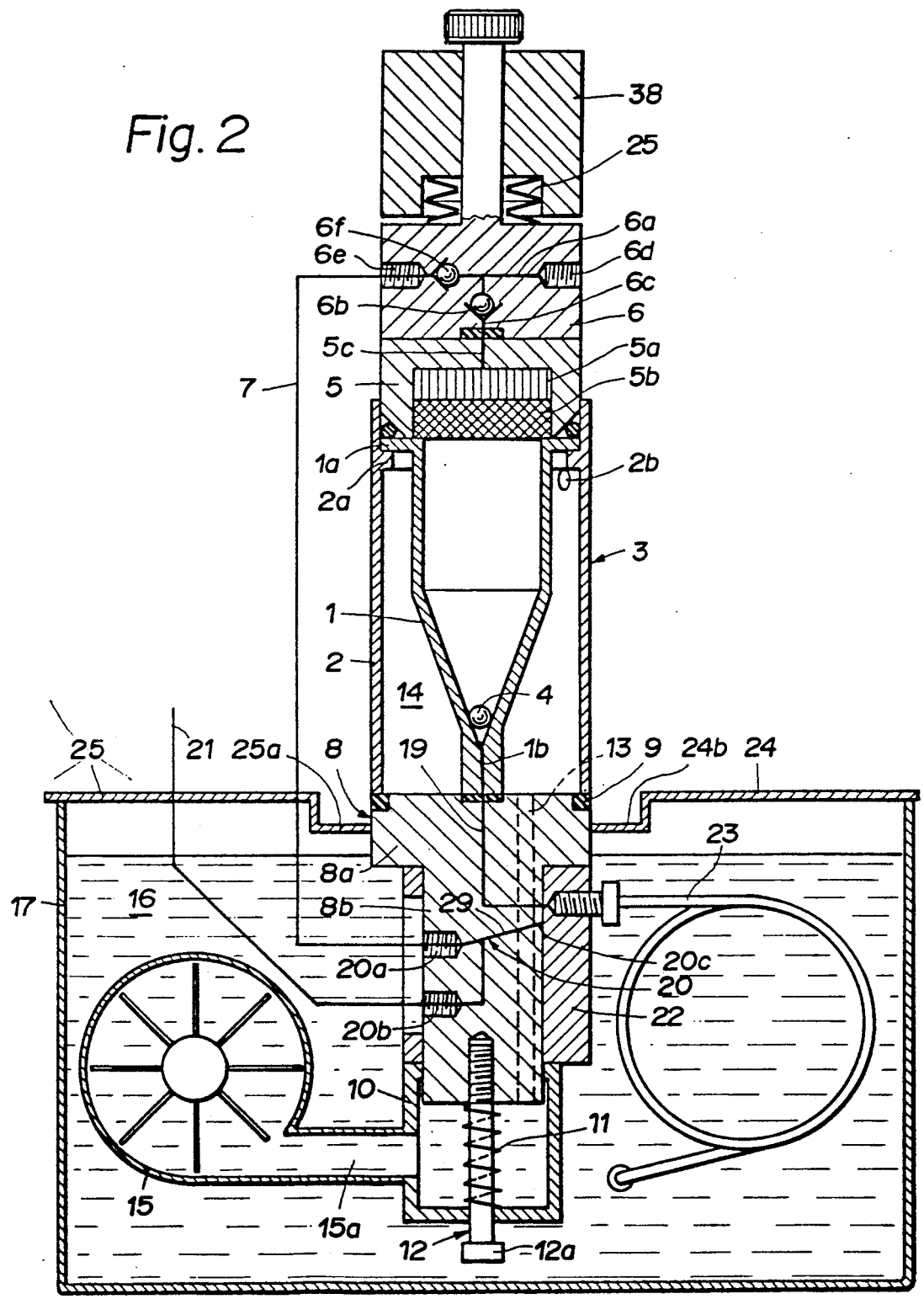
FIG. 2 is a view showing a schematic vertical section through a testing cell and cooperating parts of the apparatus.

A testing cell shown in FIGS. 2–4 is identified as a whole with reference numeral 1 and has conventional dimensions. The testing cell sits with its upper edge $1a$ on a rib $2a$ provided in the interior of a cylindrical casing 2. The tubular casing of tube 2 forms a single structural element with other tubes of the same diameter and a rectangular frame 3. The casing tube 2 has an overflow opening $2b$ to be located under the rib $2a$. The tubes together with the cells form a heating bath to maintain constant the temperature of a testing fluid accommodated in the individual cells.

The cells 1 are open from above and have below an inlet opening 1b. A ball 4 for operating a check valve prevents running out of the testing fluid. A filter head 5 is arranged on the testing cell 1. The filter head 5 contains a filter which is composed of two parts 5a and 5b glued to one another. The filter prevents backflow of undissolved particles. Conduit 5c connects the filter with a vertical conduit 6c in a closure part 6.

A check valve 6b prevents return flow of the testing fluid in the filter 5a/5b and thereby in the testing cell. A vertical conduit 6c is connected with a horizontal conduit 6a which has two ports, namely a port 6d for connecting the conduit and supplying the testing fluid, and a port 6e connected with a rinsing conduit 7. A check valve 6f prevents flowing of the testing fluid into the rinsing conduit.

Each testing cell 1 stands on a cell base 8. The base 8 has an upper round portion 8a with a diameter which corresponds to the diameter of the casing tube 2. A ring 9 prevents running out of the hot water from the hot bath.

The lower portion 8b of each cell base 8 has a square cross-section and is vertically displaceably inserted in the wall of a horizontally arranged square tube 10. The tube 10 serves as a support for the cell base 8. The lower portion 8b of the cell base 8 is pressed downwardly against the force of a spring 11 and secured during withdrawl by a head 12a of a pin 12. A vertical conduit 13 leads from the square tube 10 through the cell base into an intermediate chamber 14 between the testing cell 1 and the casing tube 2.

A schematically shown pump 15 acts for pumping hot water 16 from a container 17 thorugh a conduit 15a into the square tube 10. The container 17 accommodates a not shown heating element, a thermostat, the square tube 10 at the lower parts of the cell base 8. The hot water 16 then flows from the square tube 10 though conduits 13 into individual intermediate chambers 14 and can be used as a heating medium of the heating bath. The heating water can leave the intermediate chambers through the overflow openings 2b and flow to intermediate chamber 18 between the casing tubes 2 and a wall of the rectangular frame 3 back to the container 17.

A conduit 19 for the testing fluid opens in the upper surface of each cell base 8. In addition to the conduits 13 and 19, the cell base 8 has a further forked conduit 20. A port 20a of one conduit 20 is connected through the rinsing conduit 7 with the port 6e of the connecting part 6 while a second port 20b serves for connecting a compressed air conduits 21. A third port 20c depending on the position of a guiding sleeve 22 fixedly connected with the square tube 10 is closed or connected with a conduit 23. The conduit 23 serves for supplying a testing fluid and also the rinsing fluid through the hot water 16. The container 17 is closed from above by a cover 24. The upper surface of the cover 24 is located in the same plane as the upper surface of the cell base 8. In addition, it has a depression 24b adjoining the cell base 8 and provided with openings for the cell bases.

Figure 12:
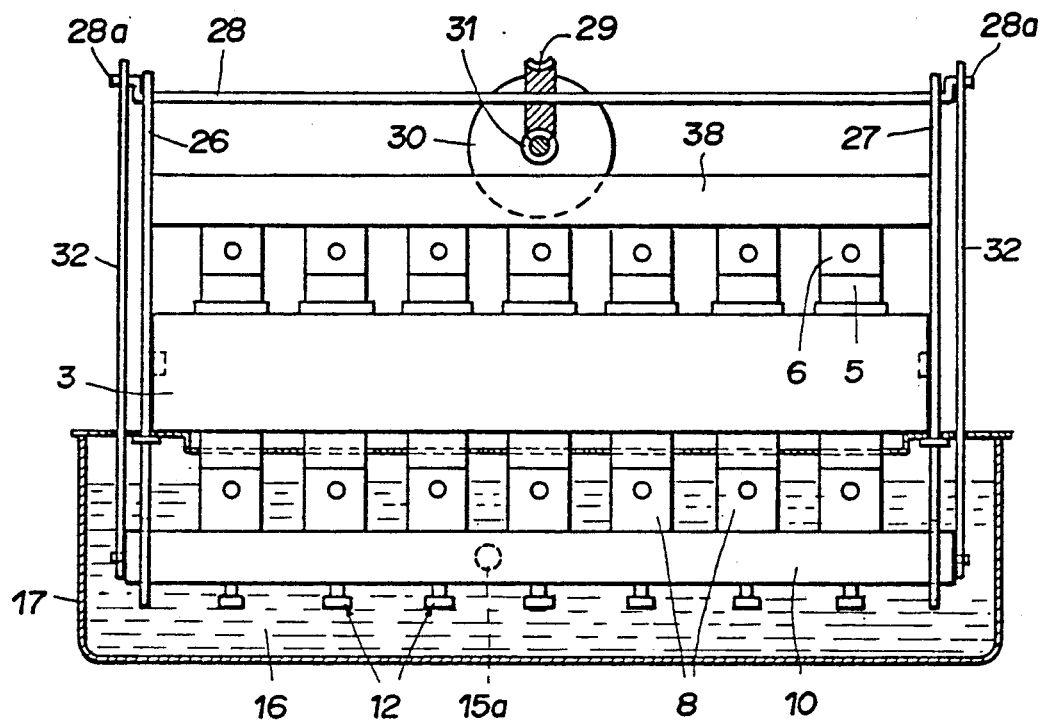
FIG. 12 is a schematic vertical section of the cell unit with a closing mechanism.

As can be seen from FIG. 12, two side walls 26 and 27 are fixedly connected with the cover 24 and have a bearing at their upper end for a crankshaft 298. A worm wheel 29 is mounted on the crankshaft 28 and engages with a worm 31 driven from a motor 30. The link 32 is suspended in each of two bent ends 28a of the crankshaft 28. The square tube 10 is suspended on the links 32.

Figure 1:
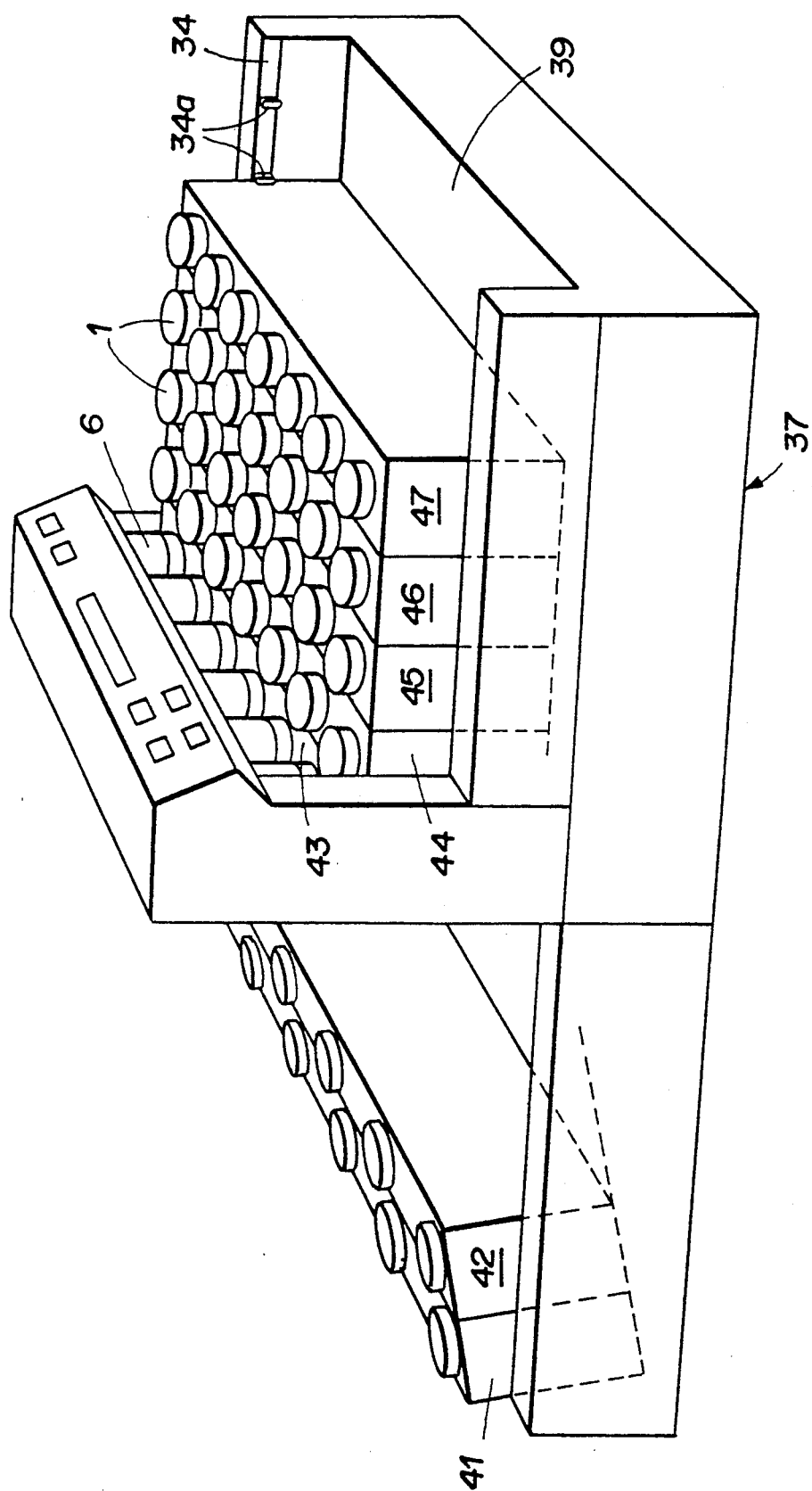
FIG. 1 is a schematic, perspective view of an apparatus for dissolution testing of solid medications in operation in accordance with the present invention.
Figure 11:
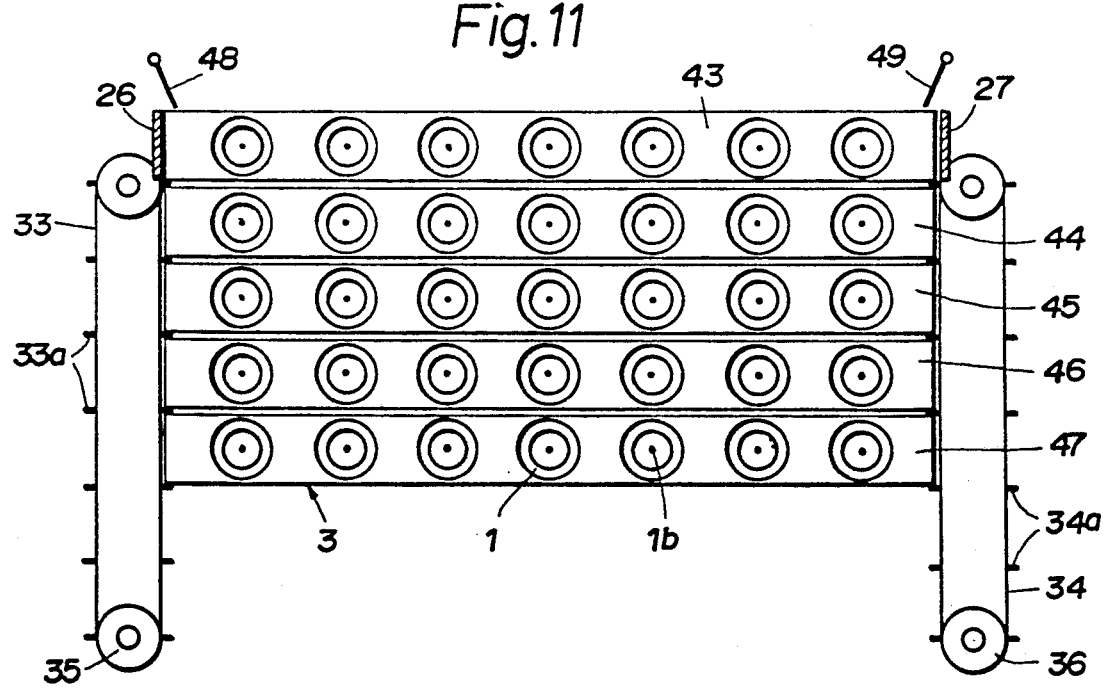
FIG. 11 is a schematic plan view of a detail of a cell pack-supply.

As can be seen from FIGS. 1 and 11, seven testing cells in the shown example identified with reference numeral 1 are assembled to a cell element or a cell pack. The seven cell packs or cell elements schematically shown in FIG. 1 are identified with 41–47.

The element 43 is located in the position which corresponds to the vertical section of FIG. 12. In this position each testing cell is screwed by the filter head 5 and fixed by the connecting member 6.

FIG. 11 schematically shows an embodiment of the device for transporting the individual cell elements from a storage place to a testing place. The device has two transporting chains or bands 33 and 34, provided with drivers 33a and 34a. Two rollers 35 and 36 which are mechanically connected with one another and driven by a joint motor, drive the bands in response to a control pulse of a control mechanism accommodated in a housing 37. A not shown end switch turns off the drive motor when the cell pack reaches its proper position on the cell base 8 under the connnecting member 6. It is elastically supported on a supporting beam 38 which is fixedly arranged in the housing 37. Instead of a control for the motor driven by the roller 35 and 36, the motor can be connected through a slipping coupling with the rollers provided with means actuatable by the control mechanism arresting the cell elements. This is identified with reference numerals 48 and 49 in the drawings.

For performing the dissolution testing the medicine to be tested is accommodated in each testing cell. This takes place in accordance with predetermined testing processes for different medication forms.

It is also possible that several such as five or more cell packs or cells elements each containing for example seven testing cells are prepared. In other words, a medication in accordance with the testing process is introduced in the testing cell 1, then the testing cells are inserted in the element composed of the casing tube 2 and the frame 3, and then the filter head 5 is placed on each testing cell. Then the thusly prepared elements are arranged on the upper side 39 as shown in FIG. 1, and put in operation by a control mechanism accommodated in the housing 37 and controlled by a timer.

After the switching on, the transporting bands 33/34 bring a first cell element such as for example the pack 43 to the working position on the cell base 8, in which the supply opening 1b of each cell 1 is located above the testing fluid supply conduit 19, and the chamber 14 serving as heating bath is located above the heating water supply conduit 13. When the pack reaches this position, the displacement is turned off preferably by the action of an end switch. Then the motor 30 is turned on and turns the crank 28 through the worm 31 and worm wheel 29 to the position shown in FIG. 12. In this position the square tube 10 assumes its uppermost position and presses the cell base 8 against the testing cell 1 so that the filter head 5 arranged on it is pressed against the connecting part 6. The connecting part 6 is displaced against the force of the spring 25 somewhat upwardly, therefore the testing cells are held fixedly and reliably, and the various conduits located over one another are connected tightly with one another.

When this position is reached, the heating water supply conduit 13 opens. This can be performed by switching over of a not shown valve or operating the heating water pump 15. It fills the intermediate chamber between the casing tube 2 and the cells 1 so that the cells are arranged in a heating bath. Through the opening 2b the heating water flows back to the container 17. By elapsing of an adjustable time which is selected so that the testing cell 1 can reach the resting temperature, the testing fluid throughflow is activated. This can be performed either by switching on of a not shown pump or by switching over the valves. The fluid flows through seven testing conduits 23 in the heating water container, where they reach the predetermined temperature. The testing fluid flows simultaneously and uniformly through the individual testing cells 1 of the clamped cell pack 43 and leaves the cells through the filter 5a/5b in the filter head. From there it flows through the conduit 6c/6a and in conduits connected to each port 6d, for example to a collecting vessel.

Either after elapsing of an adjusted test time or after passing a predetermined quantity of testing fluid, the testing fluid supply and circulation through the heating bath is shut off and the heating water flows back from the chamber 14 to the container 17. Then the motor 30 is set in operation for such a time until both bent ends 28a or in other words the cranks of the crankshaft 28 form their lowermost position. By the displacement of the square pipe 10, supply sleeve 22 which is either fixedly connected with the square tube 10 or pressed by not shown springs from the upper portion 8a of the cell base 8 downwardly, is displaced to the lower portion 8b so that the testing fluid conduit 23 is no longer connected with the conduit 13 but instead is connected with the rinsing conduit 7 through the conduit 20. By a short time throughflow of the testing fluid, the conduits 6a and the discharge conduits connected with the ports 6d are cleaned. After shutting off the throughflow to the testing fluid which serves as a rinsing fluid, the pressure air is blown through the conduit 21. The cleaning fluid is blown from the above mentioned conduits. During the downward movement the square tube 10 pulls the cell base 8 over the pins 12 thorugh these pins so that the cell pack is released upwardly from the connecting member 6 and extends downwardly on the cover 24. By the drivers 34a/35a of the transporting bands, the cell pack 43 is pushed away and the next cell pack is displaced to the now freed place. After this the motor 30 is again turned on so as to bring the square tube 10 through the crankshaft 28 and the links 26 and 27 to the position shown in the drawings. The above described process is repeated many times until the cell pack is located on the preparation position 39.

From the above description it is believed to be clear that with the inventive device it is possible to place in preparation during conventional working time so many testing cells that the testing process during several hours especially night hours withour labor force, can be performed in unattended and fully automatic manner. Therefore, on the one hand labor costs can be saved and on the other hand the research results can be obtained faster.

Within the frame of the present invention it is also possible to design the above described apparatus in somewhat different manner. With the use of a slowly running motor, it is possible instead of a screw 31 and screw wheel 29 to use two interengaging bevel gears and to arrange motor axis-parallel to the shaft 28 with the gears mounted on it and on the shaft 28. The upper end of each or both rods 32 can be provided with a thread which is rotatable by a motor and displaceable vertically on the thread so that the motor can positively displace the rods upwardly and downwardly. A further possibility is that, instead of the motor 30, the worm 31 and the worm gear 29 another drive element for example hydraulic or pneumatic cylinder-piston unit can be used for rotating the shaft 28. It is also possible to get rid of the whole mechanical drive and to dispense with the control mechanism. In this way a simple design is provided for manual operation. The worm gear 29 is replaced with a hand wheel or a lever fixedly connected with the shaft 28, which can be turned by 90° or more depending on the eccentricity of the crank.

In this case naturally the automatic supply of the cell elements is dispensed with and after a testing time the above described operation is performed manually. Especially in this case it is advantageous instead of the rinsing conduit 7 and the conduits 20 in the cell base 8 and the displaceable port for the conduit 19, to utilize a rinsing block as shown in FIGS. 7 and 8, and identified with reference numeral 40. In this case such a rinsing block is arranged between two cell packs. After shutting off the testing fluid supply to the testing cells, it flows back and a rinsing block is moved to the cell base. It is fixed in the above described manner and again the testing fluid is used as rinsing fluid for rinsing the conduit in the connecting member 6 and the conduits connected with the connecting member. After rinsing of these conduits they can be further subjected to blowing action.

It is not necessary to form the individual cells as shown in FIGS. 2, 3 and 4. As can be seen from FIGS. 5 and 6, the cells identified here with reference numeral 51 can be formed as an integral member with the cylinder casings 52. Thereby neither the above described apparatus nor the above described process is to be changed.

It is also possible to utilize the individual cells as shown in FIGS. 9 and 10. In this case, the cells can be placed on a rotary table, and then displaced in a desirable manner to their testing places on the cell bases.

It will be understood that each of the elements described above, or two or more together, may also find a useful application in other types of constructions differing from the types described above.

While the invention has been illustrated and described as embodied in a dissolution testing apparatus for medications, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus for dissolution testing of solid medications in accordance with a throughflow method, comprising a plurality of testing cells to be surrounded by heating bath each having a lower supply opening for testing fluid and an upper filter with a filter head having an outlet opening; a connecting member arranged on said filter head and tightly connectable with said outlet opening of said filter head under pressure and connected with a conduit for outflow of the testing fluid; a cell base provided with a testing fluid supply conduit and tightly placed on said supply opening of each of said testing cells; and tensioning means pressing all said connecting members and all said cell bases together on said testing cells.

2. An apparatus as defined in claim 1; and further comprising a thermostatically controlled heating water storage to release a heating water supply conduit for the heating bath.

3. An apparatus as defined in claim 1, wherein said tensioning means includes a supporting beam which supports said connecting members, a support which holds said cell bases, and a clamping device pulling said supporting beam and said support against one another and displacing the same from one another.

4. An apparatus as defined in claim 1, wherein said heating bath includes a plurality of heating bath elements, each of said heating bath elements having an overflow.

5. An apparatus as defined in claim 1, wherein some of said testing cells form a cell element.

6. An apparatus as defined in claim 5, wherein said cell element includes three said testing cells.

7. An apparatus as defined in claim 5, wherein said cell element includes at least six said testing cells.

8. An apparatus as defined in claim 5, wherein said cell element is a self-contained unit.

9. An apparatus as defined in claim 5, wherein said heating bath includes a plurality of heating bath elements arranged so that each of said testing cells of said cell element is provided with its own heating bath element.

10. An apparatus as defined in claim 9, wherein each of said testing cells with a respective one of said heating bath elements together form a self-contained unit.

11. An apparatus as defined in claim 6, wherein said testing cells of said unit are non-releasably connected with one another.

12. An apparatus as defined in claim 8, wherein said testing cells of said unit are releasably connected with one another; and further comprising means for releasably connecting said testing cells of said unit with one another.

13. An apparatus as defined in claim 12, wherein said means for releasably connecting said testing cells in said unit includes a container.

14. An apparatus as defined in claim 12, wherein said means for releasably connecting said testing cells in said unit includes a frame.

15. An apparatus as defined in claim 2; and further comprising a timer-controlled mechanism operative for controlling operation of the apparatus.

* * * * *